United States Patent [19]

Webb et al.

[11] Patent Number: 4,912,099

[45] Date of Patent: Mar. 27, 1990

[54] ACARICIDE FORMULATIONS

[75] Inventors: Michael A. Webb; Malcolm A. Faers, both of Cambridge, England

[73] Assignee: Schering Agrochemicals Limited, United Kingdom

[21] Appl. No.: 206,101

[22] Filed: Jun. 13, 1988

[30] Foreign Application Priority Data

Jun. 13, 1987 [GB] United Kingdom ............... 8713849

[51] Int. Cl.$^4$ ...................... A01N 43/00; A01N 55/04
[52] U.S. Cl. ................................... 514/183; 514/493; 514/971
[58] Field of Search ................... 514/183, 971, 493

[56] References Cited

U.S. PATENT DOCUMENTS 3,657,451 4/1988 Horne .................................. 556/88

FOREIGN PATENT DOCUMENTS 0005912 12/1979 United Kingdom ............... 424/244

OTHER PUBLICATIONS

Chem. Abst. 103:191438b (1985), Bostonian et al.

Primary Examiner—Douglas W. Robinson
Assistant Examiner—Zohreh A. Fay
Attorney, Agent, or Firm—Ostrolenk, Faber, Gerb & Soffen

[57] ABSTRACT

Aqueous compositions which comprise particulate clofentezine and an amount of fenbutatin oxide sufficient to prevent or substantially inhibit crystal growth of the clofentezine particles.

11 Claims, No Drawings

ACARICIDE FORMULATIONS

This invention concerns aqueous acaricidal compositions.

The compound 3,6-bis(2-chlorophenyl)-1,2,4,5-tetrazine, otherwise known by the common name clofentezine, is an acaricide which is active in the control of mites, particularly spider mites, in apples and other fruit crops. It is supplied initially as a concentrate formulation which is stored until required when it is diluted to the required concentration and applied to the area to be treated. One of the main concentrate formulations supplied is an aqueous suspension in which the clofentezine is present as fine particles suspended in an aqueous medium. However, this suffers from the disadvantage that some crystal growth of the clofentezine particles is observed on prolonged storage, especially under adverse conditions, eg high temperatures, and this leads to lower activity of the formulation when applied.

We have now found that the incorporation into an aqueous clofentezine formulation of a small amount of another known acaracide, namely fenbutatin oxide, ie bis[tris(2-methyl-3-phenylpropyl)tin]oxide, surprisingly prevents or substantially inhibits the observed crystal growth of the clofentezine.

Accordingly, in one aspect, this invention provides an aqueous composition which comprises particulate clofentezine and an amount of fenbutatin oxide sufficient to prevent or substantially inhibit crystal growth of the clofentezine particles.

Since fenbutatin oxide is hydrolysed reversibly in water, the stabilising effect observed may well be due to the hydrolysis product thereof, namely (2-methyl-2-phenyl-propyl)tin hydroxide. The term 'fenbutatin oxide' as used herein is accordingly meant to include this compound also.

The clofentezine is normally present in the aqueous suspension in a concentration of from 1 to 70% by weight, preferably from 5 to 60% by weight, and especially from 15 to 50% by weight. It preferably has a volume median diameter of less than 2 microns, where the volume median diameter is the particle diameter which 50% by volume of the sample exceeds.

The crystal growth of the clofentezine is found to be substantially inhibited by small amounts of fenbutatin oxide, which accordingly may be present in the aqueous suspension in an amount of as little as 0.05% by weight. The effect is observed, however, at all concentrations above this level, and it will be appreciated therefore that there is no real upper limit for its concentration, subject of course to the overall stability of the formulation. Nevertheless, we prefer the concentration of the fenbutatin oxide to be from 0.1 to 50% by weight of the formulation. Concentrations of from 0.1 to 5%, especially 0.1 to 3%, are particularly preferred.

The ratio of clofentezine to fenbutatin oxide is preferably at least 1:1 by weight, and may be up to about 800:1. The fenbutatin oxide may be present in an amount in which it exerts an acaricidal effect when the diluted composition is applied, in which case, if this is desired, higher amounts will be included in the composition than are required solely to stabilise the clofentezine. Where it is desired only to stabilise the clofentezine, however, the ratio of clofentezine to fenbutatin oxide is preferably from 10:1 to 100:1 by weight, especially from 20:1 to 70:1 by weight.

Naturally, the compositions of the invention will also contain excipients such as are normally employed to prepare them, for example suspending agents, surface active agents, deflocculating agents, anti-freeze agents and preservatives, but these in general are not directly relevant to the present invention, and may be employed in suitable quantities and ratios that are convenient and practical.

By way of general guidance, however, we prefer to include from 1 to 10%, especially from 2 to 6%, by weight of one or more surface active agents in the composition. We prefer to include from 0.5 to 5% by weight of one or more suspending and/or thickening agents. The inclusion of from 0.5 to 5% of one or more preservatives is also favoured, as is the inclusion of from 1 to 20% by weight of one or more antifreeze agents.

The compositions of the invention may of course also contain other active insecticides or acaracides, for example bifenthrin, tar oil, dicofol, methidathion, propargite, amitraz, chlorobenzilate, bromopropylate, benzoximate, binapacryl, tetradifon, formetanate, profenophos, triazophos, monocrotophos, carbophenothion, prothoate, omethoate, dioxathion, dialifos, ethion, azocyclotin, or a pyrethroid such as permethrin, cypermethrin, fenvalerate, fluorocythrin, deltamethrin, alfoxylate, phenothrin, cyphenothrin, fenpropathrin, cyhalothrin, cyfluthrin, tralomethrin, tralocythrin, esfenvalerate, fluvalinate, furamethrin, fenfluthrin, fenpyrithrin, phencyclate, tetrallethrin, pyrethrin, cinerin, jasmolin, allethrin, barthrin, dimethrin, bioallethrin, alphamethrin, tetramethrin, resmethrin, bioresmethrin, flumethrin or empenathrin.

The compositions of the invention are prepared by conventional methods known for the preparation of similar compositions. Thus, the clofentezine and fenbutatin oxide components will each be milled to an appropriate particle size (eg less than 2 microns diameter), and will be suspended in water containing the requisite amounts of the surface active agents, suspending agents and other adjuvants employed. Any further active ingredients in the formulations will be included by methods appropriate to them, for example by dissolving them in water or an emulsifiable oil if soluble therein, or by milling them to an appropriate particle size, and suspending them in water.

The invention is illustrated by the following Examples.

EXAMPLE 1

Suspension concentrate formulations were prepared each containing the following ingredients:

|  | g/l |
|---|---|
| Fenbutatin oxide | 0 or 10 or 20 |
| Clofentezine | 500 |
| Synperonic PE/P75 | 30 |
| Polyfon H | 20 |
| Monopropylene glycol | 105 |
| Dow Corning 1520 | 0.5 |
| Kelzan | 2 |
| Formalin 40% | 2 |
| Water | to 1 liter |

(NB-Synperonic PE/P75 is a propylene oxide/ethylene oxide block copolymer surface active agent, Polyfon H is a sodium lignin sulphonate dispersing agent, Dow Corning 1520 is a polydimethylsiloxane emulsion antifoam agent, Kelzan is a xanthan gum suspending agent, the monopropylene glycol is present as an antifreeze agent, and the formalin is present as a preservative).

These formulations were stored at 50° C. for 1 week, and were evaluated at the end of that period by means of a Coulter Counter to determine the volume median diameter of the particles present and also the percentage of particles present having a diameter less than 2 microns. It was found that the volume median diameter of the formulation containing no fenbutatin oxide had increased by 38% over its initial value before storage (ie to 1.7 microns from 1.3 microns), and that the percentage by volume of particles of diameter less than 2 microns had decreased by 30% relative to the initial percentage. In the formulation contaning 10 g of fenbutatin oxide, the volume median diameter increased by only 6%, and the percentage by volume of particles of diameter less than 2 microns decreased by only 2%. The corresponding results from the formulation containing 20 g of fenbutatin oxide were 7% increase in volume median diameter, and 2% decrease in the percentage by volume of particles of less than 2 microns diameter.

EXAMPLE 2

Compositions exactly analogous to those of Example 1 but containing 550 g/l of clofentezine and 0 or 10 g/l of fenbutatin oxide were prepared and stored at 50° C. for a period of 2 weeks. It was found that the volume median diameter of the particles of clofentezine in the formulation had increased by 92% (ie from 1.2 microns to 2.3 microns) and the proportion of particles under 2 microns diameter had decreased from 82 to 41% in the composition containing no fenbutatin oxide, whereas in that containing 10 g/l of fenbutatin oxide the volume median diameter increased by just 7% (from 1.4 to 1.5 microns) and the proportion of particles of diameter under 2 microns decreased only from 64 to 60%.

EXAMPLE 3

Suspension concentrates analogous to those of Example 1 were also prepared containing the following amounts of clofentezine and fenbutatin oxide:

| Clofentezine (g/l) | Fenbutatin oxide (g/l) |
|---|---|
| 10 | 1.0 |
| 10 | 3.0 |
| 10 | 10.0 |
| 10 | 30.0 |
| 10 | 50.0 |
| 50 | 1.0 |
| 50 | 3.0 |
| 50 | 10.0 |
| 50 | 30.0 |
| 50 | 50.0 |
| 100 | 1.0 |
| 100 | 3.0 |
| 100 | 10.0 |
| 100 | 30.0 |
| 100 | 50.0 |
| 200 | 1.0 |
| 200 | 3.0 |
| 200 | 10.0 |
| 200 | 30.0 |
| 200 | 50.0 |
| 500 | 1.0 |
| 500 | 3.0 |
| 500 | 30.0 |
| 500 | 50.0 |
| 700 | 1.0 |
| 700 | 3.0 |
| 700 | 10.0 |
| 700 | 30.0 |
| 700 | 50.0 |

All of the above formulations in the storage test described above in Example 1 exhibited less increase in volume median diameter and number of particles above 2 microns diameter than the corresponding control formulations containing no fenbutatin oxide.

We claim:

1. An aqueous composition which comprises particulate clofentezine and an amount of fenbutatin oxide sufficient to substantially inhibit crystal growth of the clofentezine particles, the amount being at least 0.05% and such that the ratio of clofentezine to fenbutatin oxide is up to about 800:1.

2. A composition according to claim 1 in which the clofentezine is present in an amount of from 1 to 70% by weight.

3. A composition according to claim 2 in which the clofentezine is present in an amount of from 15 to 50% by weight.

4. A composition according to claim 1, in which the clofentezine has a volume median diameter of less than 2 microns.

5. A composition according to claim 1, in which the fenbutatin oxide is present in an amount of from 0.1 to 50% by weight.

6. A composition according to claim 5 in which the fenbutatin oxide is present in an amount of from 0.1 to 5% by weight.

7. A composition according to claim 6 in which the fenbutatin oxide is present in an amount of from 0.1 to 3% by weight.

8. A composition according to claim 1 in which the ratio of clofentezine to fenbutatin oxide is from 1:1 to 800:1 by weight.

9. A composition according to claim 8 in which the ratio of clofentezine to fenbutatin oxide is from 10:1 to 100:1 by weight.

10. A composition according to claim 9 in which the ratio of clofentezine to fenbutatin oxide is from 20:1 to 70:1 by weight.

11. A composition according to claim 10 in which the clofentezine is present in an amount of from 15 to 50% by weight.

* * * * *